United States Patent
Merce-Vidal et al.

(10) Patent No.: US 6,518,295 B1
(45) Date of Patent: Feb. 11, 2003

(54) UTILIZATION OF ARYL(OR HETEROARYL) AZOLYLCARBINOL DERIVATIVES IN THE PREPARATION OF A MEDICAMENT FOR THE TREATMENT OF TROUBLES MEDIATED BY AN EXCESS OF SUBSTANCE P

(75) Inventors: Ramón Merce-Vidal; Jordi Frigola-Constansa, both of Barcelona (ES)

(73) Assignee: Laboratorios del Dr. Esteve, S.A., Barcelona (ES)

( * ) Notice: Subject to any disclaimer, the term of this patent is extended or adjusted under 35 U.S.C. 154(b) by 0 days.

(21) Appl. No.: 09/762,079

(22) PCT Filed: Aug. 5, 1999

(86) PCT No.: PCT/ES99/00255
§ 371 (c)(1),
(2), (4) Date: Feb. 1, 2001

(87) PCT Pub. No.: WO00/07542
PCT Pub. Date: Feb. 17, 2000

(30) Foreign Application Priority Data

Aug. 7, 1998 (ES) .................................. 9801708

(51) Int. Cl.$^7$ .................. A61K 31/415; A61K 31/4155; C07D 231/12
(52) U.S. Cl. .................. 514/406; 548/365.7; 548/375.1
(58) Field of Search ................. 514/326, 406; 546/211; 548/365.7, 375.1

(56) References Cited

FOREIGN PATENT DOCUMENTS

| EP | 289380 | 11/1988 |
| EP | 699674 | 3/1996 |
| WO | 9824438 | 6/1998 |
| WO | 9824439 | 6/1998 |
| WO | 9824445 | 6/1998 |
| WO | 9824447 | 6/1998 |

OTHER PUBLICATIONS

STN International R CAPLUS Database, EP 329236 Takamura et al. (abstract), RN 125001–11–8.*

* cited by examiner

*Primary Examiner*—Ceila Chang
*Assistant Examiner*—Sonya Wright
(74) *Attorney, Agent, or Firm*—Ladas & Parry

(57) ABSTRACT

The present invention relates to the use of derivatives of aryl (or heteroaryl) azolylcarbinols of general formula (1) of the specification, as well as their physiologically acceptable salts, in the manufacture of medicaments, useful in human and/or veterinary therapy, for the treatment of disorders that are mediated by an excess of substance P, and especially disorders of the central nervous system such as anxiety, depression, schizophrenia, manic depressive psychosis, sexual dysfunction, drug addiction, cognitive disorders, and locomotive disorders.

3 Claims, No Drawings

UTILIZATION OF ARYL(OR HETEROARYL) AZOLYLCARBINOL DERIVATIVES IN THE PREPARATION OF A MEDICAMENT FOR THE TREATMENT OF TROUBLES MEDIATED BY AN EXCESS OF SUBSTANCE P

This application is a 371 of PCT/ES99/00255 filed Aug. 5, 1999.

FIELD OF THE INVENTION

The present invention relates to the use of derivatives of aryl(or heteroaryl)azolylcarbinols of general formula (I), as well as their physiologically acceptable salts, in the manufacture of medicaments, useful in human and/or veterinary therapy, for the treatment of disorders that are mediated by an excess of substance P, and especially disorders of the central nervous system such as anxiety, depression, schizophrenia, manic depressive psychosis, sexual dysfuntion, drug addiction, cognitive disorders, locomotive disorders, etc.

BACKGROUND OF THE INVENTION

Substance P is a peptide, a tachykinin, that can be isolated from brain tissue and the gastrointestinal tract. In the brain, substantia nigra and the basal ganglions contain relatively high concentrations of substance P.

There is evidence suggesting that substance P functions as a neurotransmitter. In the basal ganglions, substance P is synthesised in the medium sized striatal neurones with spinae, which project the substantia nigra pars reticulate. Studies on the receptor distribution indicate that the receptors $NK_1$ are found in the striate at a relatively high density, but are to all extents and purposes absent from the substantia nigra. However, the substantia nigra contains one of the highest levels of tissue substance P in the central nervous system. Although this seems to indicate that receptor and ligand are unpaired, substance P can interact with the receptors in the striate by release of from collateral local axons of the striatonigral neurones. The terminals containing substance P have been shown to make synaptic contact with the cholinergic cell bodies in the striate. In the striate, the receptors $NK_1$ seem to be expressed mainly by cholinergic inter-neurones, although a small population of non-cholinergic striatal neurones can also express these receptors. Furthermore, stimulation of the $NK_1$ receptors by substance P has been shown to increase the release of acetylcholin (Ach), both in vitro and in vivo. As a consequence, an anatomical circuit has been described in which substance P, released locally in the striate from the collateral axons of the striatonigral neurones can bind to the $NK_1$ receptors of the striatal cholinergic inter-neurones to stimulate the release of acetylcholine (J. J. Anderson, J.Pharmacol. Exp. Ther., 1995, 274, 928–936).

Substance P has also been implicated in the pathophysiology of several neuropsychiatric disorders such as, schizophrenia, manic depressive psychosis, sexual dysfunction, drug addiction, cognitive disorders, locomotive disorders, or with depression (M. Bianchi, Inflamm. Res., 1995, 44 (11), 466–469). Similarly, a clear relation between depressive states and levels of substance P can be supposed, since the products that act as inhibitors of substance P have a clear anti-depressive component when studied in various laboratory animal models.

On the other hand, there is also a relation between the anxiety processes (anxiolisis/anxiogenesis) with the levels of substance P. It has been demonstrated that products that act as antagonists of the $NK_1$ receptor display anxiolytic activity in a social interaction trial (S. File, Pharmacol. Biochem. Behav., 1997, 58 (3), 747–752), with little tendency towards the development of tolerance. Similarly, administration of substance P is an anxiogenic agent when studied in the elevated-plus-maze trial (R. M. Teixeira, Eur.J. Pharmacol., 1996, 31 (1), 7–14), and substance P receptor blockers have the opposite effect. It can therefore be deduced that the levels of substance P play an important role in the expression of anxiety.

In our patents EP 289380 and ES 9800793 we have described carbinol derivatives of general formula (I)

(I)

wherein Ar represents a benzene ring or a substituted or unsubstituted thiopheno ring, R1 represents a hydrogen atom or a lower alkyl group ($C_1$–$C_4$); R2 represents a dialkylaminoalkyl or azahetercyclylalkyl radical and Het represents an azol, as well as their physiologically acceptable salts, which are claimed for the treatment of pain.

In our patents PCT/EP 96105596, ES 9701538, ES 9701728 and ES 9800793 we have also described several procedures for preparing enantiomerically pure compounds of general formula (I).

We have now discovered that the compound of general formula (I), as well as their physiologically acceptable salts, are especially useful in the manufacture of medicaments, useful in veterinary and/or human therapy, for the treatment of disorders that are mediated by an excess of substance P, especially certain disorders of the central nervous system such as anxiety, depression, schizophrenia, manic depressive psychosis, sexual dysfunction, drug addiction, cognitive disorders, locomotive disorders, etc.

DETAILED DESCRIPTION OF THE INVENTION

The present invention relates to the use of derivatives of aryl(or Ieteroaryl)azolylcarbinol of general formula (I)

(I)

where

Ar is a phenyl or thienyl radical, unsubstituted or optionally substituted by 1, 2 or 3 identical or different substituents, selected from the group composed of fluorine, chlorine, bromine, methyl, trifluoromethyl and methoxy;

R1 is a hydrogen atom, a cyclohexyl group, an N-methylpiperidyl group, a phenyl group, a vinyl group or a $C_1$–$C_4$ alkyl group;

R2 is a hydrogen atom or di($C_1$–$C_4$ alkyl)amino ($C_2$–$C_3$ alkyl), ($C_1$–$C_2$ alkyl)azaheterocyclyl ($C_2$–$C_3$ alkyl), or azaheterocyclyl ($C_2$–$C_3$ alkyl); and Het is a heterocyclic azotic five-membered ring that contains from one to three nitrogen atoms, unsubstituted or optionally substituted by 1 or 2 identical or different substituents selected from the group composed of fluorine, chlorine, bromine, a $C_1$–$C_{12}$ alkyl group, a benzyl radical, a cyano $C_2$–$C_3$alkyl) radical, a carboxyalkyl ($C_2$–$C_3$ alkyl) radical, a methoxycarbonyl ($C_2$–$C_3$ alkyl) radical, a hydroxy ($C_2$–$C_3$ alkyl) radical, an amino ($C_2$–$C_3$ alkyl) radical, a di($C_1$–$C_4$ alkyl)amino ($C_2$–$C_3$ alkyl) radical and an azaheterocyclyl ($C_2$–$C_3$ alkyl) radical; or one of its physiologically acceptable salts, in the manufacture of a medicament for the treatment of disorders that are produced by an excess of substance P, and specially disorders of the central nervous system involving substance P receptors such as anxiety, depression, schizophrenia, manic depressive psychosis, sexual dysfuntion, drug dependency, cognitive disorders, locomotive disorders, etc., in mammals, including man.

The term "$C_1$–$C_4$ alkyl group" represents a straight or branched radical that is derived from a saturated hydrocarbon of from 1 to 4 carbon atoms, such as methyl, ethyl, propyl, isopropyl, butyl, isobutyl, sec-butyl and terc-butyl for example.

The term "di($C_1$–$C_4$ alkyl)amino ($C_2$–$C_3$ alkyl), ($C_1$–$C_2$ alkyl)azaheterocyclyl ($C_2$–$C_3$ alkyl), or azaheterocyclyl ($C_2$–$C_3$ alkyl)" represents an alkyl radical of two or three carbon atoms joined to a di$C_1$–$C_4$ alkyl)amine or to a ($C_1$–$C_2$ alkyl)azaheterocycle or to an azaheterocycle, respectively, such as dimethylaminoethyl, dimethylaminopropyl, diethylaminoethyl, piperidylethyl, N-ethylpiperidylethyl, N-methylpyrrolidinylethyl, morpholinylpropyl, pyrrolidinylalkyl, etc.

The term "cyano ($C_2$–$C_3$ alkyl)" represents an alkyl radical of two or three carbon atoms joined to a cyano functional group.

The term "carboxy($C_2$–$C_3$ alkyl)" represents an alkyl radical of two or three carbon atoms joined to a carboxyl functional group.

The term "methoxycarbonyl($C_2$–$C_3$ alkyl)" represents an alkyl radical of two or three carbon atoms joined to a methoxycarbonyl functional group.

The term "hydroxy($C_2$–$C_3$ alkyl)" represents an alkyl radical of two or three carbon atoms joined to a hydroxyl functional group.

The term "amino($C_2$–$C_3$ alkyl)" represents an alkyl radical of two or three carbon atoms joined to an amino functional group.

The compounds of general formula (I) can be synthesised according to the procedures described in patents EP 289380 or ES 9800793. The compounds of general formula (I) have a stereogenic centre and the invention relates both to the use of a pure enantiomer and to a mixture of enantiomers. The enantiomers can be prepared by some of the procedures described in our patents PCT/EP 96/05596, ES 9701538, ES 9701728 or ES 9800793.

Examples of pharmaceutical compositions that contain compounds of general formula (I) are described in our patents EP 289380 or ES 9800793.

Illustrative examples of the compounds provided in the present invention include the compounds that are characterised by the data presented in tables 1 to 7.

TABLE 1

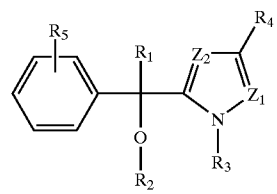

| Example No. | $R_5$ | $R_1$ | $R_3$ | $Z_1$ | $Z_2$ | $R_4$ | $R_2$ |
|---|---|---|---|---|---|---|---|
| 1 | H | H | Me | CH | N | H | DMA |
| 2 | 4-Cl | Me | Me | CH | N | H | DMA |
| 3 | 4-Cl | H | Me | CH | N | H | DMA |
| 4 | 3-Cl | H | Me | CH | N | H | DMA |
| 5 | 2-Cl | Me | Me | CH | N | H | DMA |
| 6 | 4-F | Me | Me | CH | N | H | DMA |
| 7 | 3-CF$_3$ | Me | Me | CH | N | H | DMA |
| 8 | 3-Cl | Me | Me | CH | N | H | DMA |
| 9 | 3-Cl | n-But | Me | CH | N | H | DMA |
| 10 | 4-Cl | Me | n-But | CH | N | H | DMA |
| 11 | 4-OMe | Me | Me | CH | N | H | DMA |
| 12 | 3-Cl | Me | Me | CH | N | H | Pyr |
| 13 | 3,4,5-tri-OMe | n-But | C$_{12}$H$_{25}$— | CH | N | H | DMA |
| 14 | 4-CF$_3$ | H | n-But | CH | N | H | DMA |
| 15 | 3-CF$_3$ | Me | Me | CH | N | H | Pip |
| 16 | 3,4-di-Cl | cyclohexyl-H | Me | CH | N | H | DMA |
| 17 | 3,4-di-Cl | n-But | Me | CH | N | H | DMA |
| 18 | 3,4-di-Cl | Me | Me | CH | N | H | DMA |
| 19 | 3,4-di-Cl | H | Me | CH | N | H | DMA |
| 20 | 4-Cl | Me | piperidinyl-N—(CH$_2$)$_2$— | CH | N | H | DMA |

TABLE 1-continued

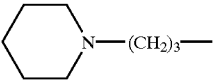

| Example No. | R₅ | R₁ | R₃ | Z₁ | Z₂ | R₄ | R₂ |
|---|---|---|---|---|---|---|---|
| 21 | 4-Cl | Me | 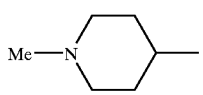 | CH | N | H | DMA |
| 22 | 4-Cl | H | N≡C—(CH₂)₃— | CH | N | H | DMA |
| 23 | 4-Cl | 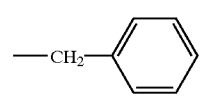 | Me | CH | N | H | DMA |
| 24 | 4-Cl | H | 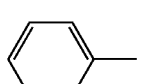 | CH | N | H | MBA |
| 25 | 4-Cl | Me | —(CH₂)₃—N(CH₃)—CH₂— | | N | H | DMA |
| 26 | 4-Cl | H | —(CH₂)₃—N(CH₃)—CH₂— | | N | H | DMA |
| 27 | H | H | n-But | N | CH | H | DMA |
| 28 | 4-Cl | 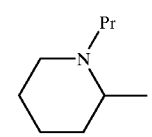 | Me | N | CH | H | DMA |
| 29 | 3,4,5-tri-OMe | H | n-But | N | CH | H | DMA |
| 30 | 4-Cl | Me | n-But | N | CH | H | DMA |
| 31 | H | H | Me | N | CH | H | DMA |
| 32 | H | Me | Me | N | CH | H | DMA |
| 33 | 3,4,5-tri-OMe | H | Me | N | CH | H | DMA |
| 34 | H | H | Me | N | CH | H | Pyr |
| 35 | H | H | Me | N | CH | H | Mor |
| 36 | 3,4,5-tri-OMe | Me | Me | N | CH | H | DMA |
| 37 | H | H | Me | N | CBr | H | DMA |
| 38 | H | Me | Me | N | CH | CH₃ | DMA |
| 39 | H | H | Me | N | CH | CH₃ | DMA |
| 40 | 2-Me | H | Me | N | CH | H | DMA |
| 41 | 4-Cl | H | Me | N | CCl | H | DMA |
| 42 | 4-Cl | H | Me | N | CH | H | DMA |
| 43 | 3-Cl | H | Me | N | CH | H | DMA |
| 44 | 4-Me | H | Me | N | CH | H | DMA |
| 45 | 2-Cl | H | Me | N | CH | H | DMA |
| 46 | H | H | Me | N | CH | H | Pip |
| 47 | H | H | Me | N | CH | H | 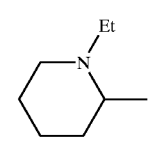 |
| 48 | H | H | Me | N | CH | H | 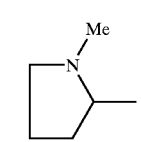 |
| 49 | H | H | Me | N | CH | H |  |

TABLE 1-continued

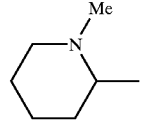

| Example No. | R₅ | R₁ | R₃ | Z₁ | Z₂ | R₄ | R₂ |
|---|---|---|---|---|---|---|---|
| 50 | H | H | Me | N | CH | H | DIPA |
| 51 | H | H | Me | N | CH | H |  |
| 52 | 4-Cl | Me | Me | CH | N | H | DMAP |
| 53 | 3-Cl | H | Me | CH | N | H | DMAP |
| 54 | 4-Cl | Et | Me | CH | N | H | DMAP |
| 55 | 3-Cl | n-But | Me | CH | N | H | DMAP |
| 56 | 4-Cl |  | Me | CH | N | H | DMAP |
| 57 | 4-F | Me | Me | CH | N | H | DMAP |
| 58 | 3-CF₃ | Me | Me | CH | N | H | DMAP |
| 59 | 2-Cl | Me | Me | CH | N | H | DMAP |
| 60 | 3-Cl | Me | Me | CH | N | H | DMAP |
| 61 | 3,4,5-tri-OMe | Me | Me | CH | N | H | DMAP |
| 62 | 4-OMe | Me | Me | CH | N | H | DMAP |
| 63 | 4-Cl | H | Me | CH | N | H | DMAP |
| 64 | 3,4,5-tri-OMe | H | Me | CH | N | H | DMAP |
| 65 | 4-CF₃ | Me | Me | CH | N | H | DMAP |
| 66 | 3-CF₃ | H | Me | CH | N | H | DMAP |
| 67 | 4-CF₃ | H | Me | CH | N | H | DMAP |
| 68 | 4-OMe | H | Me | CH | N | H | DMAP |
| 69 | 3-CF₃ | n-But | Me | CH | N | H | DMAP |
| 70 | 4-Cl | Me | n-But | CH | N | H | DMAP |
| 71 | 3,4,5-tri-OMe | n-But | n-But | CH | N | H | DMAP |
| 72 | 2-Cl | n-But | n-But | CH | N | H | DMAP |
| 73 | 2,4-di-Cl | n-But | n-But | CH | N | H | DMAP |
| 74 | 4-CF₃ | H | n-But | CH | N | H | DMAP |
| 75 | 4-Cl | H | Me | CH | N | H | PipP |
| 76 | 4-CF₃ | Me | Me | CH | N | H | PipP |
| 77 | 2-Cl | n-But | Me | CH | N | H | DMAP |
| 78 | 3,4-di-Cl | n-But | Me | CH | N | H | DMAP |
| 79 | 3,4-di-Cl | Me | Me | CH | N | H | DMAP |
| 80 | 3,4-di-Cl | H | Me | CH | N | H | DMAP |
| 81 | 3,4-di-Cl | 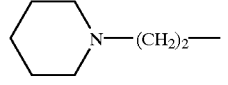 | Me | CH | N | H | DMAP |
| 82 | 4-Cl | Me | 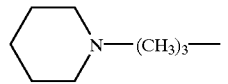 | CH | N | H | DMAP |
| 83 | 4-Cl | Me | 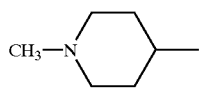 | CH | N | H | DMAP |
| 84 | 4-Cl |  | Me | CH | N | H | DMAP |
| 85 | H | H | n-But | N | CH | H | DMAP |

TABLE 1-continued

| Example No. | R₅ | R₁ | R₃ | Z₁ | Z₂ | R₄ | R₂ |
|---|---|---|---|---|---|---|---|
| 56 | 4-Cl | Me | n-But | N | CH | H | DMAP |
| 87 | H | H | Me | N | CH | H | DMAP |
| 88 | H | Me | Me | N | CH | H | DMAP |
| 89 | H | Me | Me | N | CH | Me | DMAP |
| 90 | H | H | Me | N | CH | Me | DMAP |
| 91 | 2-Me | H | Me | N | CH | H | DMAP |
| 92 | 4 Cl | H | Me | N | CH | H | DMAP |
| 93 | H | H | Me | N | CH | H | PipP |
| 94 | H | H | Me | N | CH | H | PirP |

DMA = dimethylaminoethyl
Pyr = pyrrolidinylethyl
Pip = piperidylethyl
MBA = (methyl-benzylamino)ethyl
Mor = morpholinylethyl
DIPA = diisopropylaminoethyl
DMAP = dimethylaminopropyl
PipP = piperidylpropyl
PirP = pyrrolidinylpropyl

TABLE 2

| Example No. | R₅ | R₁ | R₃ | R₂ |
|---|---|---|---|---|
| 95 | 4-Cl | H | Me | DMA |
| 96 | 4-Cl | Me | Me | DMA |
| 97 | 4-Cl | H | Me | N-piperidyl-Pr |
| 98 | 4-Cl | H | Me | 2-Me-piperidyl (N-Me) |
| 99 | 4-Cl | H | Me | 2-Et-piperidyl (N-Et) |
| 100 | 4-Cl | H | Me | DIPA |
| 101 | 4-Cl | H | Me | 2-Me-pyrrolidinyl (N-Me) |
| 102 | H | H | Me | DMAP |
| 103 | 4-Cl | H | Me | MorP |
| 104 | 4-Cl | H | Me | PirP |

DMA = dimethylaminoethyl
DIPA = diisopropylaminoethyl
DMAP = dimethylaminopropyl
MorP = morpholinypropyl
PirP = pyrrolidinylpropyl

TABLE 3

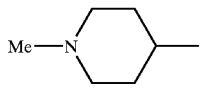

| Example No. | $R_5$ | $R_1$ | $R_3$ | $Z_1$ | $Z_2$ | $R_4$ | M.p. |
|---|---|---|---|---|---|---|---|
| 105 | H | H | H | CH | N | H | 202–3° C. |
| 106 | 4-Cl | H | H | CH | N | H | 196–7° C. |
| 107 | 4-Cl | H | Me | CH | N | H | 137–9° C. |
| 108 | 3-Cl | H | Me | CH | N | H | 126–8° C. |
| 109 | 4-F | H | Me | CH | N | H | 112–5° C. |
| 110 | 3-CF$_3$ | H | Me | CH | N | H | 125–6° C. |
| 111 | 4-CF$_3$ | H | Me | CH | N | H | 124–5° C. |
| 112 | 3,4,5-tri-OMe | H | Me | CH | N | H | 160–1° C. |
| 113 | 3,4-di-Cl | H | Me | CH | N | H | 157–9° C. |
| 114 | 4-CF$_3$ | H | n-But | CH | N | H | 111–2° C. |
| 115 | 2,4-di-Cl | H | n-But | CH | N | H | 94–7° C. |
| 116 | 4-Cl | H | n-But | CH | N | H | 108–110° C. |
| 117 | 3,4,5-tri-OMe | H | n-But | CH | N | H | 122–5° C. |
| 118 | 3,4,5-tri-OMe | H | n-dodecyl | CH | N | H | Oil |
| 119 | 3-Cl | n-But | Me | CH | N | H | 125–6° C. |
| 120 | 3-Cl | Me | Me | CH | N | H | 180–1° C. |
| 121 | 4-Cl | Me | Me | CH | N | H | 191–2° C. |
| 122 | 4-Cl |  | Me | CH | N | H | 183–4° C. |
| 123 | 4-Cl | Et | Me | CH | N | H | 166–8° C. |
| 124 | 4-Cl | n-But | Me | CH | N | H | 120–2° C. |
| 125 | 4-Cl |  | Me | CH | N | H | 161–2° C. |
| 126 | 2-Cl | Me | Me | CH | N | H | 181–2° C. |
| 127 | 2-Cl | n-But | Me | CH | N | H | 138–41° C. |
| 128 | 3-CF$_3$ | Me | Me | CH | N | H | 193–4° C. |
| 129 | 3-CF$_3$ | n-But | Me | CH | N | H | 140–1° C. |
| 130 | 3-CF$_3$ |  | Me | CH | N | H | 156–7° C. |
| 131 | 4-CF$_3$ | Me | Me | CH | N | H | 167–8° C. |
| 132 | 4-F | Me | Me | CH | N | H | 176–7° C. |
| 133 | 4-OMe | Me | Me | CH | N | H | 181–2° C. |
| 134 | 3,4-di-Cl | Me | Me | CH | N | H | 207–8° C. |
| 135 | 3,4-di-Cl | n-But | Me | CH | N | H | 142–4° C. |
| 136 | 3,4-di-Cl | 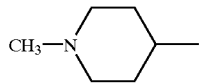 | Me | CH | N | H | 158–60° C. |
| 137 | 3,4,5-tri-OMe | CH$_3$ | Me | CH | N | H | 181–2° C. |
| 138 | 4-Cl | Me | n-But | CH | N | H | 174–5° C. |
| 139 | 4-Cl | n-But | n-But | CH | N | H | 134–5° C. |
| 140 | 4-Cl |  | n-But | CH | N | H | 184–5° C. |
| 141 | 3,4,5-tri-OMe | n-But | n-But | CH | N | H | 125–6° C. |
| 142 | 2-Cl | n-But | n-But | CH | N | H | 132–3° C. |
| 143 | 3-CF$_3$ | Et | n-But | CH | N | H | 164–5° C. |
| 144 | 2,4-di-Cl | n-But | n-But | CH | N | H | 142–3° C. |

TABLE 3-continued

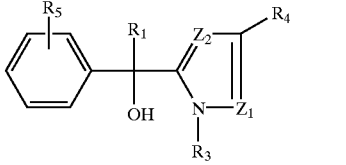

| Example No. | $R_5$ | $R_1$ | $R_3$ | $Z_1$ | $Z_2$ | $R_4$ | M.p. |
|---|---|---|---|---|---|---|---|
| 145 | 4-Cl | Me | piperidine-N—(CH$_2$)$_2$— | CH | N | H | 136–7° C. |
| 146 | 4-Cl | Me | Me$_2$N—(CH$_2$)$_3$— | CH | N | H | 147–8° C. |
| 147 | 3,4,5-tri-OMe | n-But | n-Dodecyl | CH | N | H | 75–7° C. |
| 148 | 3-CF$_3$ | n-But | Ph-CH$_2$— | CH | N | H | Oil |
| 149 | 4-Cl | Me | Ph-CH$_2$— | CH | N | H | 154–5° C. |
| 150 | 4-Cl | H | —(CH$_2$)$_2$—CN | CH | N | H | 134–5° C. |
| 151 | 4-Cl | H | —(CH$_2$)$_2$—NH$_2$ | CH | N | H | 187–8° C. |
| 152 | 3-Cl | H | —(CH$_2$)$_2$—CO$_2$H | CH | N | H | 212–3° C. |
| 153 | 4-Cl | H | —(CH$_2$)$_2$—CH$_2$OH | CH | N | H | 121–2° C. |
| 154 | 4-Cl | H | —(CH$_2$)$_2$—CO$_2$Me | CH | N | H | 96–7° C. |
| 155 | H | H | —(CH$_2$)$_2$—CH$_2$OH | CH | N | H | 110–1° C. |
| 156 | 4-Me | H | —(CH$_2$)$_2$—CH$_2$OH | CH | N | H | 104–5° C. |
| 157 | 4-OMe | H | —(CH$_2$)$_2$—CH$_2$OH | CH | N | H | Oil |
| 158 | 3,4-di-Cl | H | —(CH$_2$)$_2$—CH$_2$OH | CH | N | H | 138–9° C. |
| 159 | H | H | —(CH$_2$)$_2$—CO$_2$Me | CH | N | H | 93–6° C. |
| 160 | 4-Cl | H | —(CH$_2$)$_4$—OH | CH | N | H | 131–2° C. |
| 161 | 4-Cl | H | —(CH$_2$)$_3$—CN | CH | N | H | Oil |
| 162 | 4-Cl | H | —(CH$_2$)$_3$—CO$_2$H | CH | N | H | >300° C. |
| 163 | 4-Cl | H | —(CH$_2$)$_3$—CO$_2$Me | CH | N | H | 85–7° C. |
| 164 | H | H | n-But | N | CH | H | 47–8° C. |
| 165 | 4-Cl | H | Me | N | CH | H | 94–7° C. |
| 166 | 3,4,5-tri-OMe | H | Me | N | CH | H | Oil |
| 167 | 3,4,5-tri-OMe | H | n-But | N | CH | H | Oil |
| 168 | H | H | Me | N | CBr | H | 110–11° C. |
| 169 | 4-Cl | Ph | Me | N | CH | H | 167–8° C. |
| 170 | 4-Cl | Me | n-But | N | CH | H | Oil |
| 171 | H | Me | Me | N | CH | H | 99–100° C. |
| 172 | 3,4,5-tri-OMe | Me | Me | N | CH | H | 144–5° C. |
| 173 | H | Me | Me | N | CH | Me | 137–8° C. |
| 174 | H | CH$_2$=CH— | Me | N | CH | H | 95–6° C. |
| 175 | 4-Cl | CH$_2$=CH— | n-But | N | CH | H | 84–5° C. |
| 176 | H | H | Me | N | CCl | H | Oil |
| 177 | 2-Me | H | Me | N | CH | H | 113–4° C. |
| 178 | 3-Cl | H | Me | N | CH | H | 128–9° C. |
| 179 | 4-Me | H | Me | N | CH | H | 123–6° C. |
| 180 | 2-Cl | H | Me | N | CH | H | 96–8° C. |
| 181 | 4-OMe | H | Me | N | CH | H | 129–30° C. |

TABLE 4

| Example No. | $^1$H RMN, δ (CDCl$_3$) |
|---|---|
| 1 | 7.2(s, 5H); 6.8(d, 2H); 5.7(s, 1H); 3.5(m, 2H); 3.35(s, 3H); 2.6(t, 2H); 2.3(s, 6H) |
| 2 | 7.2(s, 4H); 6.85(d, 2H); 3.7(m, 1H); 3.2(s, 3H); 3.1(m, 1H); 2.5(t, 2H); 2.2(s, 6H); 1.85(s, 3H) |
| 3 | 7.25(s, 4H); 6.85(d, 2H); 6.65(s, 1H); 3.6(m, 2H); 3.45(s, 3H); 2.6(t, 2H); 2.25(s, 6H) |
| 4 | 7.3(m, 4H); 6.9(d, 2H); 5.7(s, 1H); 3.6(m, 2H); 3.5(s, 3H); 2.65(t, 2H); 2.35(s, 6H) |
| 5 | 7.9(m, 1H); 7.1(m, 3H); 6.8(d, 2H); 3.55(m, 1H); 3.05(s, 3H); 2.8(m, 1H); 2.4(t, 2H); 2.15(s, 6H); 2.0(s, 3H) |
| 6 | 7.0(m, 6H); 3.5(m, 2H); 3.3(s, 3H); 2.5(t, 2H); 2.3(s, 6H); 1.8(s, 3H) |
| 7 | 7.3(m, 3H); 6.8(d, 2H); 3.6(m, 2H); 3.2(s, 3H); 2.5(m, 2H); 2.2(s, 6H); 1.8(s, 3H) |
| 8 | 7.0(m, 3H); 6.8(d, 2H); 3.55(m, 2H); 3.2(s, 3H); 2.5(m, 2H); 2.2(s, 6H); 1.8(s, 3H) |
| 9 | 7.5–6.6(m, 6H); 3.55(m, 1H); 3.2(s, 3H); 3.0(m, 1H); 2.6(m, 2H); 2.2(s, 6H); 1.5–0.5(m, 7H) |
| 10 | 7.2(s, 4H); 6.9(d, 2H); 3.7(m, 3H); 3.0(m, 1H); 2.5(t, 2H); 2.25(s, 6H); 1.9(s, 3H); 1.4–0.6 (m, 7H) |
| 11 | 7.0(q, 4H); 6.75(d, 2H); 3.7(s, 3H); 3.6(m, 1H); 3.25(s, 3H); 3.0(m, 1H); 2.55(t, 2H); 2.2(s, 6H); 1.9(s, 3H) |
| 12 | 7.1(m, 6H); 3.7(m, 1H); 3.2(s, 3H); 3.05(m, 1H); 2.7(m, 2H); 2.4(m, 4H); 1.9(s, 3H); 2.75 (m, 4H) |

TABLE 4-continued

| Example No. | $^1$H RMN, δ (CDCl$_3$) |
|---|---|
| 13 | 6.9(d, 2H); 6.5(s, 2H); 3.8(s, 3H); 3.7(s, 6H); 3.55(m, 1H); 3.0(m, 1H); 2.55(t, 2H); 2.2(s, 6H); 1.3–0.7(m, 34H) |
| 14 | 7.4(s, 4H); 6.8(d, 2H); 5.8(s, 1H); 3.6(m, 4H); 2.45(t, 2H); 2.1(s, 6H); 1.6–0.5(m, 7H) |
| 15 | 7.7(s, 1H); 7.35(m, 3H); 6.9(d, 2H); 3.7(m, 3H); 3.2(s, 3H); 3.1(m, 1H); 2.6(m, 2H); 2.4(m, 4H); 1.9(s, 3H); 1.45(4H) |
| 16 | 7.5–6.7(m, 5H); 3.5(m, 1H); 3.1(s, 3H); 2.8(m, 2H); 2.4(m, 3H); 2.15(s, 6H); 2.0–0.3(m, 9H) |
| 17 | 7.5–6.7(m, 5H); 3.55(m, 2H); 3.20(s, 3H); 1.0(m, 1H); 3.5(m, 3H); 2.2(s, 6H); 1.4–0.6(m, 7H) |
| 18 | 7.4–6.7(m, 5H); 3.6(m, 2H); 3.20(s, 3H); 3.05(m, 2H); 2.5(m, 2H); 2.2(s, 6H); 1.8(s, 3H) |
| 19 | 7.6–6.7(m, 5H); 5.6(s, 1H); 3.6(m, 2H); 3.45(s, 3H); 2.6(t, 2H); 2.2(s, 6H) |
| 20 | 7.2(s, 4H); 6.95(d, 2H); 3.7(m, 3H); 3.0(m, 1H); 2.5(t, 2H); 2.2(s, 6H); 2.1(m, 6H); 1.8(s, 3H); 1.4(m, 6H) |
| 21 | 7.25(s, 4H); 6.9(d, 2H); 3.7(m, 3H); 3.1(m, 1H); 2.6(t, 2H); 2.20(s, 6H); 2.15(m, 6H); 1.9 (m, 5H) |
| 22 | 7.3(s, 4H); 6.95(d, 2H); 5.7(s, 1H); 3.95(m, 4H); 3.6(m, 2H); 2.6(t, 2H); 2.2(m, 8H); 1.9(m, 2H); 1.45(m, 6H) |
| 23 | 7.3–6.7(m, 6H); 3.5(m, 1H); 3.1(s, 3H); 2.8(m, 4H); 2.4(t, 2H); 2.15–1.0(m, 15H) |
| 24 | 7.2(s, 12H); 7.0–6.8(m, 3H); 5.7(s, 1H); 5.0(s, 2H); 3.6(m, 2H); 3.5(s, 2H); 2.6(t, 2H); 2.2 (s, 3H) |
| 25 | 7.25(m, 4H); 6.9(s, 1H); 4.0–3.0(m, 9H); 2.75(m, 2H); 2.55(t, 2H); 2.3(s, 6H); 1.9(s, 3H); 1.6–1.1(m, 3H) |
| 26 | 7.3(s, 4H); 6.8(s, 1H); 5.6(s, 1H); 4.5(m, 2H); 4.1–3.5(m, 8H); 2.8(m, 4H); 2.6(t, 2H); 2.2(d, 9H); 1.5(m, 3H) |
| 27 | 7.35(m, 6H); 5.95(m, 1H); 5.50(s, 1H); 4.05(t, 2H); 3.56(t, 2H); 2.52(t, 2H); 2.20(s, 6H); 1.75–0.7(m, 7H) |
| 28 | 7.5–7.1(m, 9H); 6.3(d, 1H); 3.45(s, 2H); 3.2(t, 2H); 2.55(t, 2H); 2.20(s, 6H) |
| 29 | 7.35(m, 1H); 6.6(m, 2H); 5.9(t, 1H); 5.45(s, 1H); 4.05(t, 2H); 3.8(m, 9H); 3.55(t, 2H); 2.6(t, 2H); 2.25(d, 6H); 1.9–07(m, 7H) |
| 30 | 7.45(m, 1H); 7.2(s, 4H); 6.3(m, 2H); 3.7(t, 2H); 3.15(t, 2H); 2.5(t, 2H); 2.25(s, 6H); 1.75(s, 3H); 1.65–0.6(m, 7H) |
| 31 | 7.2(m, 6H); 5.85(d, 1H); 5.35(s, 1H); 3.65(s, 3H); 3.4(t, 2H); 2.4(t, 2H); 2.1(s, 6H) |
| 32 | 7.45(d, 1H); 7.2(s, 5H); 6.4(d, 1H); 3.6(m, 1H); 3.4(s, 3H); 3.15(m, 1H); 2.55(t, 2H); 2.25 (s, 6H); 1.8(s, 3H) |
| 33 | 7.35(d, 1H); 6.6(s, 2H); 6.0(d, 1H); 5.45(s, 1H); 3.85(m, 12H); 3.6(t, 2H); 2.6(t, 2H); 2.25 (s, 6H) |
| 34 | 7.15–7.4(m, 6H); 5.9(s, 1H); 5.4(s, 1H); 3.65(s, 3H); 3.5(t, 2H); 2.65(t, 2H); 2.40(m, 4H); 1.65(m, 4H) |
| 35 | 7.3(m, 6H); 5.85(d, 1H); 5.4(s, 1H); 3.75(s, 3H); 3.55(m, 6H); 2.5(t, 2H); 2.35(m, 4H) |
| 36 | 7.45(d, 1H); 6.5(s, 2H); 6.35(d, 1H); 3.8(s, 3H); 3.75(s, 6H); 3.5(s, 3H); 2.5(t, 2H); 2.3(s, 6H); 1.8(s, 2H) |
| 37 | 7.45(S, 1H); 7.25(s, 5H); 5.85(s, 1H); 3.6(m, 5H); 2.6(t, 2H); 2.25(s, 6H) |
| 38 | 7.2(s, 5H); 6.15(s, 1H); 3.65(m, 1H); 3.35(s, 3H); 3.2(m, 1H); 2.5(m, 2H); 2.2(s, 9H); 1.75 (s, 3H) |
| 39 | 7.25(s, 5H); 5.7(s, 1H); 5.45(s, 1H); 3.7(s, 3H); 3.5(t, 2H); 2.6(b, 2H); 2.25(s, 6H); 2.1(s, 3H) |
| 40 | 7.4–7.0(m, 5H); 5.7(s, 1H); 5.6(s, 1H); 3.85(s, 3H); 3.5(t, 2H); 2.55(t, 2H); 2.15(s, 9H) |
| 41 | 7.5–7.0(m, 6H); 6.1(s, 1H); 3.6(m, 5H); 2.7(t, 2H); 2.2(s, 6H) |
| 42 | 7.3(m, 5H); 5.9(s, 1H); 5.5(s, 1H); 3.8(s, 3H); 3.5(t, 2H); 2.5(t, 2H); 2.2(s, 6H) |
| 43 | 7.4–7.1(m, 5H); 6.0(s, 1H); 5.5(s, 1H); 3.8(s, 3H); 3.6(t, 2H); 2.6(t, 2H); 2.2(s, 6H) |
| 44 | 7.3(s, 1H); 7.2(d, 4H); 5.9(s, 1H); 5.4(s, 1H); 3.8(s, 3H); 3.5(t, 2H); 2.5(t, 2H); 2.3(s, 3H); 2.2(s, 6H) |
| 45 | 7.7–7.1(m, 5H); 5.9(s, 1H); 5.8(s, 1H); 3.9(s, 3H); 3.6(t, 2H); 2.5(t, 2H); 2.2(s, 6H) |
| 46 | 7.2(s, 6H); 5.8(s, 1H); 5.4(s, 1H); 3.7(s, 3H); 3.5(t, 2H); 2.5(t, 2H); 2.3(s, 6H); 1.4(m, 6H) |
| 47 | 7.4(s, 6H); 6.0(s, 1H); 5.4(s, 1H); 3.7(s, 3H); 3.6(t, 2H); 3.0–1(m, 5H); 0.9(t, 3H) |
| 48 | 7.3(s, 6H); 6.0(s, 1H); 5.4(s, 1H); 3.7(s, 3H); 3.5(t, 2H); 2.8–1.1(m, 13H); 1.0(t, 3H) |
| 49 | 7.3(s, 6H); 6.0(s, 1H); 5.4(s, 1H); 3.7(s, 3H); 3.5(t, 2H); 3.0(m, 1H); 2.2–1.0(m, 1 1H) |
| 50 | 7.3(s, 6H); 6.0(s, 1H); 5.5(s, 1H); 3.7(s, 3H); 3.4(t, 2H); 2.9(m, 2H); 2.6(t, 2H); 0.95(d, 12H) |
| 51 | 7.3(s, 6H); 6.0(s, 1H); 5.5(s, 1H); 3.8(s, 3H); 3.6(t, 2H); 2.8(m, 1H); 2.3(s, 3H); 2.2–1.1(m, 12H) |
| 52 | 7.2(m, 4H); 6.85(d, 2H); 3.6(m, 1H); 3.2(s, 3H); 3.0(m, 1H); 2.4(m, 2H); 2.15(s, 6H); 1.8(s, 3H) |
| 53 | 7.2(s, 1H); 7.15(s, 3H); 6.8(d, 2H); 5.6(s, 1H); 3.55(m, 2H); 3.45(s, 3H); 2.4(m, 2H); 2.25 (s, 6H); 1.8(m, 2H) |
| 54 | 7.2(s, 4H); 6.8(d, 2H); 3.4(m, 3H); 3.1(s, 3H); 2.9(m, 1H); 2.3(m, 2H); 2.2(s, 6H); 1.8(m, 2H); 0.5(t, 3H) |
| 55 | 7.2(s, 1H); 7.0(s, 3H); 3.4(m, 3H); 3.1(s, 3H); 2.9(m, 1H); 2.3(m, 2H); 2.25(s, 6H); 1.8(m, 2H); 0.5(t, 3H) |
| 56 | 7.15(s, 4H); 6.8(d, 2H); 3.5(m, 1H); 2.7(m, 1H); 2.4(m, 4H); 2.5(s, 6H); 1.9–0.5(m, 14H) |
| 57 | 7.3–6.7(m, 6H); 3.6(m, 1H); 3.3(s, 3H); 3.1(m, 1H); 2.4(m, 2H); 2.25(s, 6H); 1.9(s, 3H); 1.85(m, 2H) |
| 58 | 7.5(m, 4H); 6.9(d, 2H); 3.5(m, 1H); 3.4(s, 3H); 3.2(m, 1H); 2.4(m, 2H); 2.2(s, 6H); 1.9(s, 3H); 1.8(m, 2H) |
| 59 | 8.0(m, 1H); 7.2(m, 3H); 6.8(d, 2H); 3.6(m, 1H); 3.1(, 3H); 2.8(m, 1H); 2.3(m, 2H); 2.2(s, 6H); 2.0(s, 3H); 1.7(m, 2H) |

TABLE 4-continued

| Example No. | $^1$H RMN, δ (CDCl$_3$) |
|---|---|
| 60 | 7.3–6.6(m, 6H); 3.5(m, 1H); 3.3(s, 3H); 3.05(m, 1H); 2.3(m, 2H); 2.15(s, 6H); 1.9(s, 3H); 1.8(m, 2H) |
| 61 | 6.85(d, 2H); 6.45(s, 2H); 3.8(s,.3H); 3.75(s,6H); 3.7(m, 1H); 3.3(s, 3H); 3.0(m, 1H); 2.4 (m, 2H); 2.25(s, 6H); 1.9(s, 3H); 1.8(m, 2H) |
| 62 | 7.2–6.5(m, 6H); 3.65(s, 3H); 3.5(m, 1H); 3.15(s, 3H); 2.9(m, 1H); 2.3(m, 2H); 2.15(s, 6H); 1.85(s, 3H); 1.8(m, 2H) |
| 63 | 7.25(s, 4H); 6.85(d, 2H); 5.65(s, 1H); 3.5(m, 2H); 3.40(s, 3H); 2.35(m, 2H); 2.2(s, 6H); 1.8 (m, 2H) |
| 64 | 6.8(d, 2H); 6.55(s, 2H); 6.6(s, 1H); 3.75(s, 9H); 3.55(m, 2H); 3.45(s, 3H); 2.3(m, 2H); 2.2 (s, 6H); 1.8(m, 2H) |
| 65 | 7.4(q, 4H); 6.85(d, 2H); 3.6(m, 1H); 3.25(s, 3H); 3.0(m, 1H); 2.4(m, 2H); 2.25(s, 6H); 1.9 (s, 3H); 1.8(m, 2H) |
| 66 | 7.6(s, 1H); 7.4(s, 2H); 6.8(d, 2H); 6.7(s, 1H); 3.6(m, 2H); 3.4(s, 3H); 2.4(m, 2H); 2.15(s, 6H); 1.9(m, 2H) |
| 67 | 7.5(q, 4H); 6.85(d, 2H); 5.65(s, 1H); 3.55(m, 2H); 3.45(s, 3H); 2.4(m, 2H); 2.25(s, 6H); 1.8 (m, 2H) |
| 68 | 7.3–6.7(m, 6H); 5.7(s, 1H); 3.8(s, 3H); 3.65(m, 2H); 3.55(s, 3H); 2.4(m, 2H); 2.25(s, 6H); 1.9(m, 2H) |
| 69 | 7.6(s, 1H); 7.4(m, 3H); 6.8(d, 2H); 3.5(m, 1H); 3.2(s, 3H); 2.9(m, 1H); 2.4(m, 2H); 2.25(s, 6H); 1.9(m, 2H); 1.5–0.5(m, 7H) |
| 70 | 7.2(s, 4H); 6.9(d, 2H); 3.6(m, 3H); 3.0(m1H); 2.3(m, 2H); 2.2(s, 6H); 1.9(s, 3H); 1.7(m, 2H); 1.5–0.5(m, 7H) |
| 71 | 6.8(d, 2H); 6.4(s, 2H); 3.75(s, 3H); 3.65(s, 6H); 3.6(m, 9H); 3.6–2.5(m, 6H); 2.2(s, 6H); 1.6–0.4(m, 16H) |
| 72 | 7.9(m, 1H); 7.15(m, 3H); 6.8(d, 2H); 3.45(m, 2H); 3.0–2.2(m, 4H); 2.2(s, 6H); 2–0.5(m, 18H) |
| 73 | 7.9(m, 1H); 7.4(m, 2H); 6.8(dd, 2H); 3.4(m, 3H); 2.7(m, 2H); 2.3(m, 3H); 2.1(d, 6H); 1.9–0.5(m, 16H) |
| 74 | 7.4(q, 4H); 6.8(d, 2H); 5.6(s, 1H); 3.5(m, 4H); 2.2(m, 2H); 2.05(s, 6H); 1.8–0.5(m, 9H) |
| 75 | 7.3(s, 4H); 6.9(d, 2H); 5.6(s, 1H); 3.4(m, 5H); 2.45(m, 6H); 2–1.2(m, 8H) |
| 76 | 7.4(q, 4H); 7.85(d, 2H); 3.6(m, 1H); 3.2(s, 3H); 3.0(m, 1H); 2.3(m, 6H); 1.9(s, 3H); 1.4(m, 8H) |
| 77 | 8.0(d, 1H); 7.2(m, 3H); 6.8(d, 2H); 3.4(m, 1H); 3.0(s, 3H); 2.8(m, 1H); 2.3(m, 4H); 2.15(s, 6H); 1.8–0.5(m, 9H) |
| 78 | 7.4–6.6(m, 5H); 3.4(m, 1H); 3.2(s, 3H); 2.9(1H); 2.3(m, 4H); 2.15(s, 6H); 1.9–0.5(m, 2H) |
| 79 | 7.3(m, 2H); 6.8(m3H); 3.6(m, 1H); 3.2(s, 3H); 2.9(m, 1H); 2.3(m, 4H); 2.2(s, 3H); 1.8(s, 3H) |
| 80 | 7.5–6.9(m, 3H); 6.8(d, 2H); 5.6(s, 1H); 3.5(m, 2H); 3.4(s, 3H); 2.3(m, 2H); 2.1(s, 6H); 1.8 (m, 2H) |
| 81 | 7.6–6.7(m, 5H); 3.4(m, 1H); 2.7(m, 1H); 2.4(m, 4H); 2.15(s, 6H); 1.9–0.3(m, 14H) |
| 82 | 7.1(s, 4H); 6.95(s, 1H); 6.85(s, 1H); 3.6(m, 4H); 2.3(m, 4H); 2.1(s, 6H); 2.05(m, 4H); 1.8 (m, 6H); 1.3(m, 8H) |
| 83 | 7.2(s, 4H); 6.9(s, 1H); 6.85(m, 4H); 2.3(m, 4H); 2.1(s, 6H); 2.05(m, 4H); 1.0(m, 6H); 1.4(m, 10H) |
| 84 | 7.2–6.6(m, 6H); 3.4(m, 1H); 3.1–2.5(m, 8H); 2.15–1.5(m, 14H); 1.0(m, 4H) |
| 85 | 7.25(m, 6H); 5.9(m, 1H); 5.4(s, 1H); 3.95(t, 2H); 3.40(t, 2H); 2.25(t, 2H); 2.1(s, 6H); 1.85–0.5(m, 9H) |
| 86 | 7.45(d, 1H); 1.2(s, 4H); 6.3(s, 1H); 3.8(m, 3H); 3.1(m, 1H); 2.35(t, 2H); 2.15(s, 6H); 1.8(s, 3H); 1.9–0.6(m, 9H) |
| 87 | 7.3(s, 6H); 5.95(d, 1H); 5.45(s, 1H); 3.75(s, 3H); 3.5(t, 2H); 2.35(t, 2H); 2.15(s, 6H); 1.8 (m, 2H) |
| 88 | 7.4(d, 1H); 7.2(s, 5H); 6.35(d, 1H); 3.55(m, 2H); 3.4(s, 3H); 2.35(t, 2H); 2.2(s, 6H); 1.95–1.6(m, 5H) |
| 89 | 7.15(s, 5H); 6.0(s, 1H); 3.4(m, 1H); 3.25(s, 3H); 3.0(m, 1H); 2.2(m, 11H); 1.6(m, 5H) |
| 90 | 7.3(s, 5H); 5.75(s, 1H); 5.35(s, 1H); 3.7(s, 3H); 3.45(t, 2H); 2.35(t, 2H); 2.15(s, 9H); 1.75 (m, 2H) |
| 91 | 7.4–7.1(m, 5H); 5.7(s, 1H); 5.5(s, 1H); 3.8(s, 3H); 3.5(t, 2H); 2.3(m, 2H); 2.2(s, 9H); 1.8(m, 2H) |
| 92 | 7.4–7.2(m, 5H); 5.9(s, 1H); 5.4(s, 1H); 3.7(s, 3H); 3.5(t, 2H); 2.3(m, 2H); 2.15(s, 6H); 1.8 (m,2H) |
| 93 | 7.3(s, 6H); 6.0(s, 1H); 5.4(s, 1H); 3.7(s, 3H); 3.5(t, 2H); 2.3(m, 6H); 1.9(m, 2H), 1.5(m, 6H) |
| 94 | 7.3(b, 6H); 6.0(b, 1H); 5.4(b, 1H); 3.7(s, 3H); 3.6(m, 2H); 2.5(m, 6H); 1.8(m, 6H) |
| 95 | 7.2(s, 5H); 7.0(s, 1H); 3.75(s, 3H); 3.35(t, 2H); 2.4(t, 2H); 2.1(s, 6H) |
| 96 | 7.2(m, 6H); 3.7(s, 3H); 3.25(t, 2H); 2.4(t, 2H); 2.15(s, 6H); 1.7(s, 3H) |
| 97 | 7.3(s, 5H); 7.1(s, 1H); 5.2(s, 1H); 3.7(s, 3H); 3.45(m, 2H); 2.9–1.0(m, 17H); 0.8(t, 3H) |
| 98 | 7.3(s, 5H); 7.1(s, 1H); 5.2(s, 1H); 3.8(s, 3H); 3.5(t, 2H); 2.7(m, 1H); 2.2(m, 3H); 2.1–1.0(m, 9H) |
| 99 | 7.3(s, 5H); 7.1(s, 1H); 5.3(s, 1H); 3.5(t, 2H); 2.8–1.1(m, 13H); 1.0(t, 3H) |
| 100 | 7.3(s, 5H); 7.1(s, 1H); 5.3(s, 1H); 3.8(s, 3H); 3.4(t, 2H); 3.0(m, 2H); 2.7(t, 2H); 1.0(d, 12H) |
| 101 | 7.3(s, 5H); 7.1(s, 1H); 5.3(s, 1H); 3.8(s, 3H); 3.5(m, 2H); 3.0(m, 1H); 2.3(s, 3H); 2.2–1.2 (m, 8H) |
| 102 | 7.3(b, 6H); 7.1(s, 1H); 5.3(s, 1H); 3.7(b, 3H); 3.7–3.3(m, 2H); 2.3(m, 2H); 2.2(b, 6H); 1.8 (m, 2H) |
| 103 | 7.3(b, 5H); 7.1(s, 1H); 5.2(s, 1H); 3.8(s, 3H); 3.6(m, 6H); 2.4(m, 6H); 1.9(m, 2H) |
| 104 | 7.3(b, 5H); 7.1(s, 1H); 5.3(s, 1H); 3.8(s, 3H); 3.5(m, 2H); 2.5(m, 6H); 1.8(m, 6H) |

TABLE 4-continued

| Example No. | ¹H RMN, δ (CDCl₃) |
|---|---|
| 118 | 6.8(d, 2H); 6.5(s, 2H); 4.6(b, 1H); 3.7(m, 11H); 2.4(m, 2H); 1.5–0.6(m, 22H) |
| 148 | 7.9–6.1(m, 10H); 4.9(m, 1H); 2.5(t, 2H); 1.5–0.5(m, 9H) |
| 161 | 8.0(b, 1H); 7.2(s, 4H); 6.8(s, 1H); 5.9(s, 1H); 5.2(s, 1H); 4.8(t, 2H); 2.3–1.6(m, 4H) |
| 166 | 7.3(d, 1H); 6.5(s, 2H); 5.9(s, 1H); 5.7(s, 1H); 3.6(m, 12H) |
| 167 | 7.2(d, 1H); 6.5(s, 2H); 5.9(s, 1H); 5.7(s, 1H); 3.7(m, 11H), 1.7–0.4(m, 7H) |
| 176 | 7.3(s, 6H); 5.8(s, 1H); 3.6(m, 5H); 2.6(t, 2H); 2.3(s, 6H) |

TABLE 5

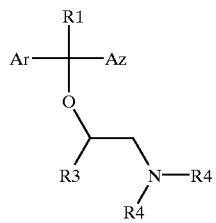

| Example | Haz | Ara | R1 | R3 | R4 | Base or Salt | M.p. (° C.) | ¹H RMN(Mhz)(Solvent)δ | IR, cm⁻¹ |
|---|---|---|---|---|---|---|---|---|---|
| 182 | 1,5-dimethylpyrazol-3-yl | 2-thienyl | H | H | CH₃ | base | oil | (300Mhz)(CDCl₃)2.24(s, 6H), 2.54(t, J=6 Hz, 2H), 3.58(m, 2H), 3.79(s, 3H), 5.76(s, 1H), 6.17(d, J=1.8Hz, 1H), 6.83(m, 1H) 6.93(m, 1H), 7.28(m, 1H), 7.38(d, J=1.8 Hz, 1H). | (film)2944, 2863, 2821, 2771, 1457, 1100, 1092, 1066, 1056, 1042, 705, 651. |
| 183 | 1,5-dimethylpyrazol-3-yl | 2-thienyl | H | H | CH₃ | citrate | 115–116 | (300Mhz)(DMSO-d₆)2.51(AB system, J=15Hz, 2H), 2.71(AB system, J=15Hz, 2H), 2.66(s, 6H), 3.18(s, 2H), 3.70–3.80(a.c., 5H, (δ=3.74, s)), 6.07(s, 1H), 6.16(s, 1H), 7.01(m, 1H), 7.10(m, 1H), 7.34(s, 1H), 7.57(m, 1H). | (KBr)3300–2300 (broad), 1732, 1589, 1475, 1398, 1380, 1356, 1220, 1203, 1183. |
| 184 | 1,5-dimethylpyrazol-3-yl | 3-methylthien-yl | H | H | CH₃ | base | oil | (300Mhz)(CDCl₃)2.24(s, 6H), 2.54(t, J=6 Hz, 2H), 3.56(m, 2H), 3.77(s, 3H), 5.59(s, 1H), 6.08(d, J=1.8Hz, 1H), 6.99(dd, J=5 Hz, J'=1.2Hz, 1H), 7.19(m, 1H), 7.30(dd, J=5Hz, J'=3Hz, 1H), 7.37(d, J=1.8Hz, 1H). | (film)2942, 2819, 2769, 1456, 1103, 783, 753. |
| 185 | 1,2-dimethylimidazol-4-yl | 2-thienyl | H | H | CH₃ | base | oil | (300Mhz)(CDCl₃)2.24(s, 6H), 2.56(m, 2H), 3.54(m, 1H), 3.56(s, 3H), 3.67(m, 1H), 5.90(s, 1H), 6.77(m, 1H), 6.85(d, J=1.2 Hz, 1H), 6.93(m, 1H), 6.98(d, J=1.2Hz, 1H), 7.27(m, 1H). | (film)2943, 2864, 2820, 2770, 1496, 1456, 1278, 1103, 1056, 772, 702. |
| 186 | 1,5-dimethylpyrazol-3-yl | 3-methylthien-2-yl | H | H | CH₃ | base | oil | (300Mhz)(CDCl₃)2.14(s, 3H), 2.23(s, 6H), 2.54(t, J=6Hz, 2H), 3.59(m, 2H), 3.84(s, 3H), 5.74(s, 1H), 6.04(s, 1H), 6.80(d, J=5.0Hz, 1H), 7.18(d, J=5.0Hz 1H), 7.33(s, 1H). | (film)2944, 2865, 2821, 2772, 1455, 1100, 1092, 1067, 1055, 1042, 782, 715. |
| 187 | 1,5-dimethylpyrazol-3-yl | 2,5-dimethylthien-3-yl | H | H | CH₃ | base | oil | (300Mhz)(CDCl₃)2.24(s, 6H), 2.43(s, 3H) 2.53(t, J=6Hz, 2H), 3.56(m, 2H), 3.80(s, 3H), 5.65(s, 1H), 6.17(d, J=1.5Hz, 1H), 6.57(d, J=2.4Hz, 1H), 6.62(d, J=2.4Hz, 1H), 7.37(d, J=1.5Hz, 1H). | (film)2944, 2863, 2820, 2772, 1456, 1286, 1101, 1092, 1067, 1055, 1042, 798, 783, 762, 652. |
| 188 | 1,5-dimethylpyrazol-3-yl | 2-bromo-5-methylthien-3-yl | H | H | CH₃ | base | oil | (300Mhz)(CDCl₃)2.25(s, 6H), 2.55(t, J=6 Hz, 2H), 3.57(m, 2H), 3.80(s, 3H), 5.68(s, 1H), 6.20(d, J=2.1Hz, 1H), 6.56(d,J=4 Hz, 1H), 6.90(d, J=4Hz, 1H), 7.40(d, J= 2.1Hz, 1H). | (film)2943, 2864, 2821, 2772, 1441, 1101, 1093, 1066, 1055, 1042, 968, 793, 761, 651. |

TABLE 5-continued

[Structure: Ar—C(R1)(Az)—O—CH(R3)—CH2—N(R4)(R4)]

| Example | Haz | Ara | R1 | R3 | R4 | Base or Salt | M.p. (° C.) | ¹H RMN(Mhz)(Solvent)δ | IR, cm⁻¹ |
|---|---|---|---|---|---|---|---|---|---|
| 189 | 1,5-dimethylpyrazol-3-yl | 5-bromothien-2-yl | H | H | $CH_3$ | base | oil | (300Mhz)($CDCl_3$)2.23(s, 6H), 2.53(t, J=5.7Hz, 2H), 3.57(m, 2H), 3.78(s, 3H), 5.72 (s, 1H), 6.18(d, J=2.1Hz, 1H), 6.74(d, J=1.5Hz, 1H), 7.19(d, J=1.5Hz, 1H), 7.39(d, J=2.1Hz, 1H). | (film)2944, 2864, 2821, 2772, 1456, 1344, 1101, 1093, 1056, 1042, 780. |
| 190 | 1,5-dimethylpyrazol-3-yl | thien-2-yl | $CH_3$ | H | $CH_3$ | base | oil | (300Mhz)($CDCl_3$)1.91(s, 3H)2.26(s, 6H), 2.52(m, 2H), 3.17(m, 1H), 3.59(m, 1H), 3.63(s, 3H), 6.31(d, J=1.5Hz, 1H), 6.58 (m, 1H), 6.88(m, 1H), 7.21(m, 1H), 7.41(d, J=1.5Hz, 1H). | (film)2940, 2819, 2770, 1456, 1369, 1235, 1108, 1041, 930, 699. |
| 191 | 1,5-dimethylpyrazol-3-yl | phenyl | H | H | $CH_3$ | citrate | 138–142 | (300Mhz)(DMSO-$d_6$)2.51(d, J=15.1Hz, 2H), 2.59(d, J=15.1Hz, 2H), 2.66(s, 6H), 3.17(t, 2H), 3.59(quint, 1H), 3.71(quint, 1H), 3.76(s, 3H), 5.76(s, 1H), 5.95(d, 1H), 7.32(d, 1H), 7.39(m, 5H). | (KBr)3300–2300 (broad), 1732, 1587, 1475, 1399, 1382, 1256, 1220, 1202, 1183. |
| 192 | 1,5-dimethylpyrazol-3-yl | phenyl | H | $CH_3$ | $CH_3$ | base | oil | (300Mhz)($CDCl_3$)1.15(d, J=6.1Hz, 3H), 2.18(s, 6H), 2.20(m, 1H), 2.57(dd, J=12.7 Hz, J'=7.3Hz, 1H), 3.65(m, 1H), 3.85(s, 3H), 5.92(m, 2H), 7.26–7.37(a.c., 6H) | (film)2970, 2941, 2821, 2768, 1451, 1095, 1073, 1049, 724, 702 |
| 193 | 1,5-dimethylpyrazol-3-yl | phenyl | H | $CH_3$ | $CH_3$ | base | oil | (300Mhz)($CDCl_3$)1.19(d, J=6.3Hz, 3H), 2.20(s, 6H), 2.30(dd, J=12.7Hz, J'=5.4 Hz, 1H), 2.53(dd, J=12.7Hz, J'=6.3Hz, 1H), 3.68(m, 1H), 3.75(s, 3H), 5.84(s, 1H), 6.07(d, J=2Hz, 1H), 7.28–7.36(a.c., 5H), 7.38(d, J=2Hz, 1H) | (film)2972, 2941, 2821, 2768, 1454, 1096, 1074, 1043, 724, 703 |

TABLE 6

[Structure: Ar—C(R1)(Az)—O—CH2—CH2—N(CH3)(CH3)]

| Example | Az | Ar | R1 | Base or Salt | Optic isomer. | Enantiomeric purity % | Specific rotation [α]$_D$ | M.p. (° C.) |
|---|---|---|---|---|---|---|---|---|
| 194 | 1,5-dimethylpyrazol-3-yl | thien-2-yl | H | base | (+) | 99 | +31.8 (c = 2.0 $CH_2Cl_2$) | oil |

TABLE 6-continued

| Example | Az | Ar | R1 | Base or Salt | Optic isomer. | Enantiomeric purity % | Specific rotation [α]$_D$ | M.p. (° C.) |
|---|---|---|---|---|---|---|---|---|
| 195 | 1,5-dimethylpyrazol-3-yl | 2-thienyl | H | base | (−) | 98.5 | −31.8 (c = 2.0 CH$_2$Cl$_2$) | oil |
| 196 | 1,5-dimethylpyrazol-3-yl | 2-thienyl | H | citrate | (+) | 99 | +2.8 (c = 2.0 MeOH) | 121–122 |
| 197 | 1,5-dimethylpyrazol-3-yl | 2-thienyl | H | citrate | (−) | 98.5 | −2.3 (c = 2.0 MeOH) | 121–122 |
| 198 | 1,5-dimethylpyrazol-3-yl | 2-thienyl | H | (D)-ditoluoyl-tartrate | (+) | 99 | +87.5 (c = 2.0 MeOH) | 130–131 |
| 199 | 1,5-dimethylpyrazol-3-yl | 2-thienyl | H | (L)-ditoluoyl-tartrate | (−) | 98.5 | −85.4 (c = 2.0 MeOH) | 130–131 |
| 200 | 1,5-dimethylpyrazol-3-yl | 3-methylphenyl | H | citrate | (+) | 99.1 | +12.3 (c = 1.0 MeOH) | 130–131 |
| 201 | 1,5-dimethylpyrazol-3-yl | 3-methylphenyl | H | citrate | (−) | 99.0 | −12.2 (c = 1.0 MeOH) | 129–131 |

TABLE 7

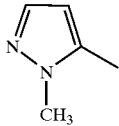

| Example | Az | Ar | R1 | Base or Salt | M.P. (° C.) | ¹H RMN(Mhz)(Solvent)δ | IR, cm⁻¹ |
|---|---|---|---|---|---|---|---|
| 202 | 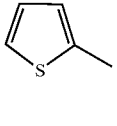 | 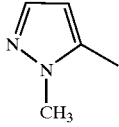 | H | base | oil | (300Mhz)(CDCl$_3$)3.67(s, 3H), 5.00(d, J= 4.5Hz, 1H), 6.06(d, J=4.5Hz, 1H), 6.16(s, 1H), 6.84(m, 1H), 6.94(m, 1H), 7.23(s, 1H), 7.27(d, J=5.1Hz, 1H). | (film)3210(broad), 1433, 1400, 1284, 1201, 1055, 1037, 1003, 781, 760, 706. |
| 203 | 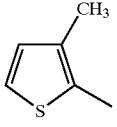 | 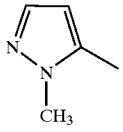 | H | base | 109–111 | (300Mhz)(CDCl$_3$)2.19(s, 3H), 2.63(d, J=4.5Hz, 1H), 3.82(s, 3H), 6.13(d, J=4.5Hz, 1H), 6.16(d, J=1.5Hz, 1H), 6.83(d, J=5.1 Hz, 1H), 7.20(d, J=5.1Hz, 1H), 7.37(d, J=1.5Hz, 1H). | (KBr) 3199(oil), 1400, 1282, 1200, 1060, 998, 940, 796, 776, 732. |
| 204 | 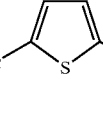 | 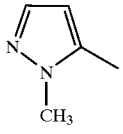 | H | base | 131–132 | (300Mhz)(CDCl$_3$)2.46(s, 3H), 2.79(d, J=4.6Hz, 1H), 3.80(s, 3H), 6.04(d, J=4.6Hz, 1H), 6.25(d, J=1.8Hz, 1H), 6.62(d, J=3.3 Hz, 1H), 6.70(d, J=3.3Hz, 1H), 7.39(d, J=1.8Hz, 1H). | (KBr)3163(broad), 3100, 1282, 1206, 1025, 1010, 801, 788. |
| 205 | 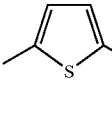 | 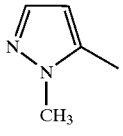 | H | base | 107–109 | (300Mhz)(CDCl$_3$)3.76(s, 3H), 3.86(b.a., 1H), 6.02(s, 1H), 6.20(d, J=1.8Hz, 1H), 6.61(d, J=4.0Hz, 1H), 6.91(d, J=4.0Hz, 1H), 7.32(d, J=1.8Hz, 1H). | (KBr)3170(broad), 3104, 1440, 1395, 1205, 1181, 1025, 1011, 966, 800, 791. |
| 206 | 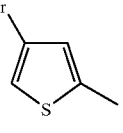 | 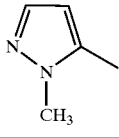 | H | base | 95–6 | (300Mhz)(CDCl$_3$)3.60(b.a., 1H), 3.78(s, 3H), 6.08(s, 1H), 6.20(d, J=1.8Hz, 1H), 6.80(s, 1H), 7.21(s, 1H), 7.35(d, J=1.8Hz, 1H). | (KBr)3112(broad), 1397, 1343, 1205, 1182, 1132, 1052, 823, 795, 768. |
| 207 | 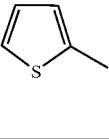 | | CH$_3$ | base | 130–131 | (300Mhz)(CDCl$_3$)2.00(s, 3H), 3.27(b.a., 1H), 3.68(s, 3H), 6.26(d, J=2.0Hz, 1H), 6.68(m, 1H), 6.91(m, 1H), 7.23(m, 1H), 7.32(d, J=2.0Hz, 1H). | (KBr)3264(broad), 1384, 1221, 1159, 1114, 802, 779, 707. |

In the present invention the activity of the compounds of general formula (I) has been demonstrated experimentally in the claimed applications, by means of a study of the in vivo effect on the release of substance P and also in two in vivo trials of anti-depressive activity.

In the following examples some properties object of the invention are indicated for the (±)-5-{α-[2-(dimethylamino) ethoxy]benzyl}-1-methyl-1H-pyrazol citrate (example 191).

The examples that are now described, presented by way of illustration, described some biological trials and should in no way be considered to limit the scope of the invention.

EXAMPLE 1
Effect on the Spinal Release of Substance P in Rats:

The study was carried out in vivo, in rats anaesthetised with halothane. The trial consisted of intrathecal perfusion with an artificial cerebrospinal fluid, with a view to collecting the peptides released from the superficial layers of the spinal cord while the product under study is administered locally or systematically. The method used was that described by Collin, E. and co-workers (*Naunyn-Schmiedeberg's Arch. Pharmacol.*, 1994, 349, 387–393).

The activity of the (±)-5-{α-[2-(dimethylamino)ethoxy] benzyl}-1-methyl-1H-pyrazol citrate (example 191) was studied, administered intrathecally in the perfusion liquid, at a concentration of 1 μM. As is summarised in table 8, the product inhibited the release of substance P. The systematic administration of 46 mg/kg of product also reduced the release of substance P.

It is of note that the effect of the systematic administration of product on the intrathecal release of substance P lasted 2 hours, the average inhibition being 50% of the effect during this period.

EXAMPLE 2
Study of the Anti-depressive Activity:

The anti-depressive activity of the (±)-5-{α-[2-(dimethylamino)ethoxy] benzyl}-1-methyl-1H-pyrazol citrate (example 191) was studied and demonstrated in two different trials in mice. In one the inhibition of ptosis induced by reserpine was studied, and in the other the effect on mobility in adverse situation was investigated.

2.1 Inhibition of Ptosis Induced by Reserpine in Mice:

The method used was that described by S.Garattini and co-workers (*Med. Exp.*, 1960, 3, 315–320). The trial consists of observing the possible inhibition of ptosis induced by reserpine (25 mg/kg, ip: intraperitoneal) in mice, after the products under study had been administered orally.

The activity of the (±)-5-{α-[2-(dimethylamino)ethoxy]benzyl}-1-methyl-1H-pyrazol citrate (example 191) administered orally at different doses has been determined. As is summarised in table 9, the (±)-5-{α-[2-(dimethylamino)ethoxy]benzyl}-1-methyl-1H-pyrazol citrate (example 191) has been shown to have clear anti-depressive activity inhibiting the effects of reserpine with a good dose-response.

2.2 Effect on Mobility in Adverse Situation:

The method used was described by R. D. Porsolt and co-workers (*Arch. Int. Pharmacodyn.*, 1987, 288, 11–30). The trial consists of suspending the mice by their tales for six minutes in an ITEMATIC-TST apparatus, which measures the mobility and the strength of the animals' movements. The animals exposed to this adverse situation, after a start with vigorous activity, become desperate and end up staying still. The products with anti-depressive activity significantly reduce the time of immobility.

As is summarised in table 10, the (±)-5-{α-[2-(dimethylamino)ethoxy] benzyl}-1-methyl-1H-pyrazol citrate (example 191) has clearly been active in this trial, reducing the immobility period significantly and in a dose-dependent fashion.

The pharmacological trials carried out show that the (±)-5-{α-[2-(dimethylamino)ethoxy] benzyl}-1-methyl-1H-pyrazol citrate (example 191), as an example of the properties object of the invention, display clear activity as inhibitor of the release of substance P, which bestows on it an application in the treatment of central nervous system disorders in which release of substance P is implicated. Furthermore, and by way of example, the anti-depressive activity has been demonstrated it two different trials carried out on experimental animals.

TABLE 8

Effect of citrate (±)-5-{α-[2-(dimethylamino)ethoxy]benzyl}-1-methyl-1H-pyrazol (example 191) on the intrathecal release of substance P.

| Treatment with example 191 | % Inhibition, with respect to control, of intrathecal release of substance P |
|---|---|
| 1 μM, intrathecal | −58% |
| 46 mg/kg, ip | −50% |

TABLE 9

Inhibition of ptosis induced by reserpine in mice.

| Product | Dose* (mg/kg, oral) | % Activity | SD-50 |
|---|---|---|---|
| Example 191 | 92 | 84 | 38.5 mg/kg, oral |
| | 80 | 75 | |
| | 23 | 30 | |
| | 12 | 8 | |

*Dose expressed in mg/kg of the base of the compound of example 191

TABLE 10

Inhibition of immobility time in adverse situation in mice.

| Product | Dose (mg/kg, oral) | % Inhibition | DE-50 |
|---|---|---|---|
| Example 191 | 92 | 69 | 50.5 mg/kg, oral |
| | 46 | 41 | |
| | 23 | 30 | |
| | 12 | 20 | |

What is claimed is:

1. A method for treating anxiety, depression, schizophrenia, manic depressive psychosis. sexual dysfunction, drug addiction, cognitive disorder, or locomotive disorder in a mammal comprising administering a therapeutically effective amount of a compound of the formula

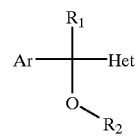

where $R^1$ is hydrogen, $R^2$ is diimethylaminoethyl, Ar is phenyl or thienyl, and Het is

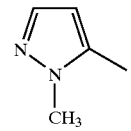

in a free base or a physiologically acceptable salt thereof.

2. The method of claim 1 wherein the salt is a physiologically acceptable salt.

3. The method of claim 1 wherein the compound is selected from the group consisting of:
   5-{α-[2-(dimethylamino)ethoxy]-2-thienylmethyl}-1-methyl-1H-pymzol,
   5-{α-[2-(dimethylamino)ethoxy]-2-thienylmethyl}-1-methyl-1H-pyrazol citrate,
   5-{α-[2-(dimethylamino)ethoxy]-3thienylmethyl}-1-methyl-1H-pyrazol,
   5-{α-[2-(dimethylamino)ethoxy]-benzyl}-1-methyl-1H-pyrazol,
   5-{α-[2-(dimethylamino)ethoxy]benzyl}-1-methyl-1H-pyrazol citrat,
   (+)-5-{α-[2-(dimethylamino)ethoxy]-2-thienylmethyl}-12-methyl-1H pyrazol,
   (−)-5-{α-[2-(dimethylamino)ethoxy]-2-thienylmnethyl}-1-methyl-1H-pyrazol,
   (+)-5-{α-[2-(dimethylamino)ethoxy]-2-thienylmethyl}-1-methyl-1H-pyrazol citrate,
   (−)-5-{α-[2-(dimethylamino)ethoxy]-2-thienylmethyl}-1-methyl-1H pyrazol citrate,
   (+)-5-{α-[2-(dimethylamino)ethoxyl]-2-thionylmethyl}-1-methyl-1H pyrazol D-diyoluoyltartrate,
   (−)-5-{α-[2-(dimethylamino)ethoxyl]-2-thienylmethyl}-1-methyl-1H pyrazol L-ditoluoyltartrate,
   (+)-5-{α-[2-(dimethylamino)ethoxyl]benzyl}-1-methyl-1H-pyrazol citrate, and
   (−)-5-{α-[2-(dimethylamino)ethoxy]benzyl}-1-methyl-1H-pyrozol citrate or a salt or entaniomer thereof.

* * * * *